United States Patent [19]
Tokiwa et al.

[11] Patent Number: 6,066,492
[45] Date of Patent: May 23, 2000

[54] MICROORGANISM CAPABLE OF DEGRADING POLYLACTIC ACID RESIN AND METHOD OF DEGRADING POLYLACTIC ACID RESIN USING SAID MICROORGANISM

[75] Inventors: Yutaka Tokiwa, Tsuchiura; Hiroyuki Jikuya, Tsukuba; Naoko Nagai, Kameoka, all of Japan

[73] Assignees: Director-General of Agency of Industrial Science and Technology, Tokyo; Shimadzu Corp., Kyoto, both of Japan

[21] Appl. No.: 09/233,041

[22] Filed: Jan. 20, 1999

Related U.S. Application Data

[62] Division of application No. 08/942,361, Oct. 2, 1997, Pat. No. 5,925,556.

[30]     Foreign Application Priority Data

Oct. 2, 1996 [JP] Japan ..................................... 8-262073
Oct. 2, 1996 [JP] Japan ..................................... 8-262074

[51] Int. Cl.⁷ .............................. C12N 1/20; A01N 63/00
[52] U.S. Cl. ...................... 435/253.5; 435/262; 435/886; 424/93.43
[58] Field of Search ...................... 424/93.43; 435/253.5, 435/262

[56]     References Cited
FOREIGN PATENT DOCUMENTS 9-37776  2/1997  Japan .

OTHER PUBLICATIONS

Sawada et al., "An evaluation of a new lactic acid polymer drug delivery system: a preliminary report", British Journal Plastic Surgery, 1994, 47, pp. 158–161.

Torres de Dominguez et al., "Bioconversion de l'Amidon en acide L–lactique, synthese chimique du poly(acide lactique) degradation par des microorganismes", Les Colloques. Inst. Natl. Rech Agron (1995), 71(Valorisations Non–Alimentaires des Grandes Produ.

Lamde et al., "Pathogenicity of *Staphylococus lugdumensis*, *Staphylococcus schleiferi*, and three other congulase–negative staphylococci in a mouse model and possible virulence factors", Can. J. Microbiol. (1990), vol. 36, pp. 455–463.

Williams D.F., "Enzymatic hydrolysis of polylactic acid", Engineering in Medecine, 1981, vol. 10, No. 1, pp. 5–7.

Bergey's Manual of Systematic Bacteriology. Williams & Wilkins. 1989, vol. 4, pp. 2462, 2470, 2474–2476.

Zimmermann et al., FEMS Microbiology Letters 1988, vol. 55, pp. 181–186.

*Primary Examiner*—Sandra E. Saucier
*Assistant Examiner*—Vera Afremova
*Attorney, Agent, or Firm*—Birch, Stewart, Kolasch & Birch, LLP

[57]     ABSTRACT

A microorganism belonging to the genus Staphylococcus or the genus Streptomyces which is capable of degrading a polylactic acid resin. A method of degrading a polylactic acid resin including a step of culturing a microorganism capable of degrading a polylactic acid resin in a medium containing a polylactic acid resin. In particular, the microorganisms *Streptomyces violaceusniger* FERM BP-6110 and *Streptomyces cyaneus* FERM BP-6111 are used.

6 Claims, 5 Drawing Sheets

MICROORGANISM CAPABLE OF DEGRADING POLYLACTIC ACID RESIN AND METHOD OF DEGRADING POLYLACTIC ACID RESIN USING SAID MICROORGANISM

This application is a divisional of application Ser. No. 08/942,361, filed on Oct. 2, 1997, now U.S. Pat. No. 5,925,556, the entire contents of which are hereby incorporated by reference.

BACKGROUND OF THE INVENTION

1. Field of the Invention

The present invention relates to a microorganism capable of degrading a polylactic acid resin and a method of degrading a polylactic acid resin by a novel biological treatment using the above microorganism.

2. Discussion of the Related Art

In recent years, disposal of plastic wastes has been of great concern. Although burning and landfill are major methods of disposal, biodegradation is drawing attention, since these conventional methods are problematic, in that, for instance, burning accelerates global warming, and landfill site availability is decreasing. Also, as a new-generation plastic material, a polylactic acid resin is now being developed for various applications; it is very likely that disposal of the polylactic acid resin waste will pose a difficult problem as with currently used plastics in the near future.

A polylactic acid resin, a polymer that undergoes hydrolysis in aqueous systems, is currently applied to medicines and medical materials. Because the polylactic acid can be synthesized via lactic acid fermentation from recyclable resources, such as starch, it is being remarked as a biodegradable plastic material as a substitute for general-purpose plastics, which are difficult to degrade under environment conditions. The polylactic acid resins occur in the form of a poly-L-lactic acid, a poly-D-lactic acid, a poly-DL-lactic acid or copolymers with other polymers, depending on the kind of constituent monomer.

The polylactic acid resin is known to undergo enzymatically accelerated hydrolysis. However, there have been no known arts regarding microorganisms capable of directly biodegrading a polylactic acid resin or wastes thereof. Also, there have been no known arts regarding methods of degrading a polylactic acid resin using microorganisms.

Accordingly, an object of the present invention is to provide a microorganism capable of directly biodegrading a polylactic acid resin or plastics containing it.

Another object of the present invention is to provide a method of degrading a polylactic acid resin using the above microorganism.

These and other objects of the present invention will be apparent from the following description.

SUMMARY OF THE INVENTION

The present inventors have made extensive investigation in view of solving the above problems, and have found bacteria, actinomycetes and other microorganisms possessing excellent degrading activity of a polylactic acid by microbiological means. The present inventors have made further investigation based on these findings, and have developed the present invention.

Accordingly, the present invention provides a method of degrading a polylactic acid resin comprising the step of degrading a polylactic acid using a microorganism, such as a bacterium or an actinomycete. More specifically, the present invention provides a method of degrading a polylactic acid resin comprising steps of adding a polylactic acid resin and a microorganism, such as a bacterium belonging to the genus Staphylococcus or an actinomycete belonging to the genus Streptomyces, to a medium containing mineral salts, culturing the microorganism, and degrading the polylactic acid resin.

BRIEF DESCRIPTION OF THE DRAWINGS

FIGS. 4($a$) and 4($b$) each is a scanning electron micrograph, showing the degradation of a piece of film with FERM BP-6109, wherein 4($a$) shows the surface conditions of the piece of film after 40 days from initiation of cultivation without microorganisms, and wherein 4($b$) shows the surface conditions of the piece of film after 40 days from initiation of cultivation of FERM BP-6109; and FIGS. 5($a$) and 5($b$) each is a scanning electron micrograph, showing the degradation of a piece of film with FERM BP-6110, wherein 5($a$) shows the surface conditions of the piece of film after 40 days from initiation of cultivation without microorganism, and wherein 5($b$) shows the surface conditions of the piece of film after 40 days from initiation of cultivation of FERM BP-6110.

DETAILED DESCRIPTION OF THE INVENTION

The term polylactic acid resin used in the present specification refers to a polymer based on lactic acid, including polylactic acid homopolymers such as poly-L-lactic acids and poly-D-lactic acids, poly-L/D-lactic acid copolymers, polylactic acid copolymers resulting from copolymerization of these polymers with other polymers, blends of the above-mentioned polymers, and blends with other component polymers, wherein the ratio by weight of the lactic acid component in the polymer is not lower than 10%.

The present invention enables degradation of a polylactic acid resin under aerobic conditions by allowing a bacterium, actinomycete or other microorganism capable of degrading the polylactic acid resin to degrade the polylactic acid resin.

Microorganisms capable of degrading a polylactic acid resin are bacteria and actinomycetes. The bacteria include the microorganisms listed in Tables 1-1 through 1-4; the actinomycetes include the microorganisms listed in Table 1-5.

TABLE 1-1

| Genera of Bacteria | |
|---|---|
| RHODOSPIRILLACEAE | POLYANGIACEAE |
| Rhodospirillum | POlyangium |

TABLE 1-1-continued

Genera of Bacteria

| | |
|---|---|
| Rhodopseudomonas | Nannocystis |
| Rhodomicrobium | Chondromyces |
| CHROMATIACEAE | CYTOPHAGACEAE |
| | |
| Chromatium | Cytophaga |
| Thiocystis | Flexibacter |
| Thiosarcina | Herpetosiphon |
| Thiospirillum | Flexithrix |
| Thiocapsa | Saprospira |
| Lamprocystis | Sporocytophaga |
| Thiodictyon | BEGGIATOACEAE |
| | |
| Thiopedia | Beggiatoa |
| Amoebobacter | Vitreoscilla |
| Ectothiorhodospira | Thioploca |
| CHLOROBIACEAE | SIMONSIELLACEAE |
| | |
| Chlorobium | Simonsiella |
| Prosthecochloris | Alysiella |
| Chloropseudomonas | LEUCOTRICHACEAE |
| | |
| Pelodictyon | Leucothrix |
| Clathrochloris | Thiothrix |
| MYXOCOCCACEAE | ACHROMATIACEAE |
| | |
| Myxococcus | Achromatium |
| Archangiaceae | RHIZOBIACEAE |
| | |
| Archangium | Rhizobium |
| CYSTOBACTERACEAE | Agrobacterium |
| | |
| Cystobacter | |
| Melittanguim | |
| Stigmatella | |

TABLE 1-2

Genera of Bacteria

| | |
|---|---|
| SPIROCHAETACEAE | HALOBACTERIACEAE |
| | |
| Spirochata | Halobacterium |
| Cristispira | Halococcus |
| Treponema | Alcaligenes |
| Borrelia | Acetobacter |
| Leptospira | Brucella |
| SPIRILLACEAE | Bordetella |
| | |
| Spirillum | Francisella |
| Campylobacter | Thermus |
| Bdellovibrio | ENTEROBACTEERIACEAE |
| | |
| Microcyclus | Escherichia |
| Pelosigma | Edwardsiella |
| Brachyarcus | Citrobacter |
| PSEUDOMONADACEAE | Salmonella |
| | |
| Pseudomonas | Shigella |
| Xanthomonas | Klebsiella |
| Zoogloea | Enterobacter |
| Gluconobacter | Hafnia |
| AZOTOBACTERACEAE | Serratia |
| | |
| Azotobacter | Proteus |
| Azomonas | Yersinia |
| Beijerinckia | Erwinia |
| Derxia | VIBRIONACEAE |
| | |
| PELONEMATACEAE | Vibrio |
| | |
| Pelonema | Aeromanaas |
| Achroonema | Plesiomonas |
| Peloploca | Photobacterium |
| Desmanthos | Lucibacterium |

TABLE 1-2-continued

Genera of Bacteria

| | |
|---|---|
| METHYLOMONADACEAE | Zymonas |
| | |
| Methylomonas | Chromobacterium |
| Methylococcus | Flavobacterium |
| | Haemophilus |
| | Pasteurella |
| | Actinobacillus |

TABLE 1-3

Genera of Bacteria

| | |
|---|---|
| Cardiobacterium | Thiobacillus |
| Streptobacillus | Sulfolobus |
| Calymmatobacterium | Thiobacterium |
| BACTEROIDACEAE | Macromonas |
| | |
| Bacteroides | Thiovulum |
| Fusobacterium | Thiospira |
| Leptotrichia | SIDEROCAPSACEAE |
| | |
| Desulfovibrio | Siderocapsa |
| Butyrivibrio | Naumaniella |
| Succinivibrio | Ochrobium |
| Succinimonas | Siderococcus |
| Lachnospira | METHANOBACTERIACEAE |
| | |
| Selenomonas | Methanobacterium |
| NEISSERIACEAE | Methanosarcina |
| | |
| Neisseria | Methanococcus |
| Branhamella | MICROCOCCACEAE |
| | |
| Moroxella | Micrococcus |
| Acinetobacter | Staphylococcus |
| Paracoccus | Planococcus |
| Lampropedia | STREPTOCOCCACEAE |
| | |
| VEILLONELLACEAE | Streptococcus |
| | |
| Veillonella | Leuconostoc |
| Acidaminococcus | Pediococcus |
| Megasphaera | Aerococcus |
| NITROBACTERACEAE | Gemella |
| | |
| Nitrobacter | PERPTOCOCCACEAE |
| | |
| Nitrospina | Peptococcus |
| Nitrococcus | Peptostreptococcus |
| Nitrosomonas | Ruminococcus |
| Nitrosospira | Sarcina |
| Nitrosococcus | |
| Nitrosolobus | |

TABLE 1-4

Genera of Bacteria

| | |
|---|---|
| BACILLACEAE | Metallogenium |
| | |
| Bacillus | Caulococcus |
| Sporolactobacillus | Kusnezovia |
| Clostridium | Nevskia |
| Desulfotpmaculum | Planctomyces |
| Sporosarcina | |
| Oscillospira | |
| LACTOBACILLACEAE | |
| | |
| Lactobacillus | |
| Listeria | |
| Erysipelothrix | |
| Caryophanon | |

TABLE 1-4-continued

Genera of Bacteria

OTHER GENERA

Sphaerrotius
Leptothrix
Streptothrix
Leiskeella
Phragmidiothrix
Crenothrix
Clonothrix
Hyphomicrobium
Hyphomonas
Pedomicrobium
Caulobacter
Asticcacaulis
Ancalomicrobium
Prosthecomicrobium
Thiodendron
Pasteuria
Blastobacter
Seliberia
Gallionella

TABLE 1-5

Genera of Actinomycetes

| ACTINOBACTERIA | ACTINOPLANETES | MICROPOLYPORAS |
|---|---|---|
| Agromyees | Actinoplanes | Actinopolyspora |
| Aureobacterium | Ampullariella | Amycoiate |
| Clavibacter | Catellatosppora | Amycolatopssis |
| Curtobacterium | Dactylosporangium | Kibdelosporanggium |
| Microbacterium | Micromonospora | Psseudonocardia |
| Arthrobacter | Pilineria | Saccharomonospora |
| Micrococcus | MADUROMYCETES | Saccharopolyspora |
| Renibacterium | Actinomadura pusilla | Facaia |
| Rothia | Microbispora | THERMO- |
| Stomatoccus | Planobispolu | PMONOSPORAS |
| Cellulomonas | Planomonospora | Actinomadura madurae |
| Oerskovia | Streptosporangium | Actinosynnnenia |
| Promicromonospora | NOCARDIOFORMS | Microtetrasppora viridis |
| Arcanobacterium | Caseobacter | Nocardiopsis |
| Actinomyces | Corynebacterium | Saccharothrix |
| Arachnia | Mycobacterium | Streptoalloteichhus |
| Pinelobacter | Rhodococcus | Thermomonospora |
| Mycobacterium | Nocardia | NOCARDIOIDES |
| Dermatophilus | MULTILOCULAR | Nocardioides |
| Brevibacterium | SPORANGIA | OTHER GENERA |
| STREPTOMYCETES | Frankia | Glycomyces |
| Intrasporangium | Geodernatophilus | Kitnsatosporia |
| Kineosporia | | Spirillosppora |
| Sporichthya | | Thermoactinomyces |
| Streptomyces | | |
| Streptoverticillium | | |

Of the microorganisms listed, bacteria belonging to the genus Staphylococcus (FERM BP-6108, FERM BP-6109) and actinomycetes belonging to the genus Streptomyces (FERM BP-6110, FERM BP-6111) are preferred. The microorganisms FERM BP-6110 and FERM BP-6111 were deposited on Sep. 19, 1996 at the National Institute of Bioscience and Human-Technology, Agency of Industrial Science and Technology, 1–3, Higashi 1-chome, Tsukuba-shi, Ibaraki-ken, 305-8566, Japan. These microorganisms are isolated as follows:

Samples are taken form soil, river water and lake water for microorganism isolation from Tsukuba City, Ibaraki Prefecture, Japan, which samples are then subjected to the procedures described in detail below to isolate aerobes that degrade the polylactic acid resin.

An agar plate medium containing 1.5% agar is prepared by emulsifying 1,000 mg of the polylactic acid resin in 1 liter of the basal medium shown in Table 2 below. Each 1-gram sample is suspended in 5 ml of sterile water and dilutes 10 to $10^2$ folds, after which a 0.2 ml portion is applied over the medium prepared. Cultivation is conducted in an incubator at 30° C. or 50° C. for bacteria or at 30° C. for actinomycetes. Out of the colonies that grow on the medium, those with a transparent zone therearound are each fished using a platinum loop to isolate a microorganism capable of degrading a polylactic acid resin.

TABLE 2

Composition of Basal Medium

| $Na_2MoO_4.2H_2O$ | 0.5 mg |
|---|---|
| $Na_2WO_4.2H_2O$ | 0.5 mg |
| $MnSO_4$ | 0.5 mg |
| $FeSO_4.7H_2O$ | 10 mg |
| NaCl | 10 mg |
| $CaCl_2.2H_2O$ | 20 mg |
| $(NH_4)_2SO_4$ | 1000 mg |
| $MgSO_4.7H_2O$ | 200 mg |
| $K_2HPO_4$ | 1600 mg |
| $KH_2PO_4$ | 200 mg |
| Detergent | 100 mg |
| Yeast Extract | 100 mg |
| Distilled Water | 1 L |
| pH | 7.0 |

Out of the colonies that grow on the medium, those found to have a transparent area therearound are each fished using a platinum loop, and subjected to pure isolation using a medium of the same composition; two bacteria (FERM BP-6108, FERM BP-6109) and two actinomycetes (FERM BP-6110, FERM BP-6111), all capable of degrading a polylactic acid resin, are obtained as isolates.

The strains isolated are inoculated to nutrient broth and allowed to colonize; the cells obtained are microscopically examined for microbiological and biochemical properties. The results are shown in Tables 3 through 6.

TABLE 3

| Strain | Staphylococcus (FERM BP-6108) |
|---|---|
| Colony Morphology | Spherule, cream color, 1 mm in diameter |
| Gram Staining | + |
| Spore Formation | − |
| Motility | − |
| Aerial Mycelium | − |
| Growth at: | |
| 30° C. | + |
| 37° C. | + |
| 50° C. | − |
| Catalase | + |
| Oxidase | − |
| OF Test | + |
| Glucose | + |
| Maltose | + |
| Mannose | + |
| Raffinose | − |
| Trehalose | + |
| Fructose | + |
| Xylose | − |
| Sucrose | + |
| Mannitol | + |

TABLE 3-continued

| | |
|---|---|
| Lactose | − |
| Melibiose | − |

TABLE 4

| | |
|---|---|
| Strain | Staphylococcus (FERM BP-6109) |
| Colony Morphology | Spherule, white color, 1 mm in diameter |
| Gram Staining | + |
| Spore Formation | − |
| Motility | − |
| Aerial Mycelium | − |
| Growth at: | |
| 30° C. | − |
| 37° C. | − |
| 50° C. | + |
| Catalase | + |
| Oxidase | − |
| OF Test | + |
| Glucose | + |
| Maltose | + |
| Mannose | + |
| Raffinose | − |
| Trehalose | − |
| Fructose | + |
| Xylose | − |
| Sucrose | + |
| Mannitol | − |
| Lactose | + |
| Melibiose | − |

TABLE 5

| | |
|---|---|
| Strain | Streptomyces (FERM BP-6110) |
| Colony Morphology | Spherule, cream color, 4–5 mm in diameter |
| Gram Staining | Variable |
| Spore Formation | − |
| Motility | − |
| Aerial Mycelium | + |
| Growth at: | |
| 30° C. | + |
| 37° C. | + |
| 50° C. | − |
| Catalase | (+) |
| Oxidase | + |
| OF Test | − |

Remarks (+): Weak positive reaction

TABLE 6

| | |
|---|---|
| Strain | Streptomyces (FERM BP-6111) |
| Colony Morphology | Spherule, cream color, 4 mm in diameter |
| Gram Staining | + |
| Spore Formation | − |
| Motility | − |
| Aerial Mycelium | + |
| Growth at: | |
| 30° C. | + |
| 37° C. | + |
| 50° C. | − |
| Catalase | (+) |

TABLE 6-continued

| | |
|---|---|
| Oxidase | − |
| OF Test | − |

Remarks (+): Weak positive reaction

The results shown in Tables 3 through 6 are assessed with reference to "Bergey's Manual of Determinative Bacteriology (9th edition)" and other references. Of the above-mentioned strains, FERM BP-6108, FERM BP-6109, FERM BP-6110 and FERM BP-6111 are identified as *Staphylococcus homimis, Staphylococcus epidermidis, Streptomyces violaceusniger* and *Streptomyces cyaneus*, respectively, judging from the fact that the two bacteria had properties similar to those of the microorganisms of the genus Staphylococcus, and that the two actinomycetes have properties similar to those of the microorganisms belonging to the genus Streptomyces.

The microorganisms of the present invention are therefore preferably those of the genus Staphylococcus and the genus Streptomyces. The microorganisms usable in the method of degrading a polylactic acid resin in the present invention are desirably a group of microorganisms including these strains.

A strain of the present invention or a group of microorganisms including said strain are used to treat a polylactic acid resin in various forms prepared as necessary, including lyophilized powder, tablets prepared by tableting a blend of the powder, various vitamins and minerals and other necessary nutrients, and culture solution obtained by culturing said strain or a group of microorganisms in the above-described basal medium.

The method of degrading a polylactic acid resin in the present invention comprises the step of culturing a microorganism capable of degrading the polylactic acid resin as described above in a medium containing the polylactic acid resin. Specifically, a polylactic acid resin can be degraded by contacting the microorganism of the present invention therewith in the medium. The basal medium used for cultivation in the degradation method of the present invention contains a nitrogen source, e.g., ammonium sulfate, ammonium phosphate or ammonium carbonate, and commonly used mineral salt nutrients, such as potassium primary phosphate, potassium secondary phosphate, magnesium sulfate, sodium chloride, ferrous sulfate, sodium molybdate, sodium tungstate and manganese sulfate, its pH being 4.0 to 10.0, preferably 5.0 to 8.0. Culturing temperature is usually 10° to 60° C., preferably 30° to 50° C., for the microorganisms of the genus Staphylococcus, or usually 10° to 47° C., preferably 10° to 40° C., for the microorganisms of the genus Streptomyces.

Although it is desirable that the biodegradation of a polylactic acid resin treatment in the present invention be conducted by adding to a cultivation tank the basal medium described above, the polylactic acid resin to be treated, the above-described powder, tablets or culture solution formulated with one of the above-described strains or a group of microorganisms, and culturing the microorganism, said strain may be incorporated in activated sludge or compost. The amount of the polylactic acid resin added to the basal medium is desirably 0.01 to 10% by weight. Although even very small amount of the microorganism added may be sufficient, it is preferable that the amount of powder, tablets or culture solution formulated with a strain or a group of microorganisms be not less than 0.01% by weight relative to the polylactic acid resin.

The method of degrading a polylactic acid resin in the present invention is useful as a method of treating polylactic acid resin wastes, and is very valuable in waste treatment because it does not produce exhaust gas as in conventional burning, and because it saves a great deal of time in comparison with landfill disposal.

Also, the method of degrading a polylactic acid resin in the present invention in compost making facilities enables the conversion of a polylactic acid resin to manure and useful substances, such as organic acids.

EXAMPLES

The present invention will be described in further detail by the following working examples, without intending to limit the scope of the present invention thereto.

Example 1

Figure 1:
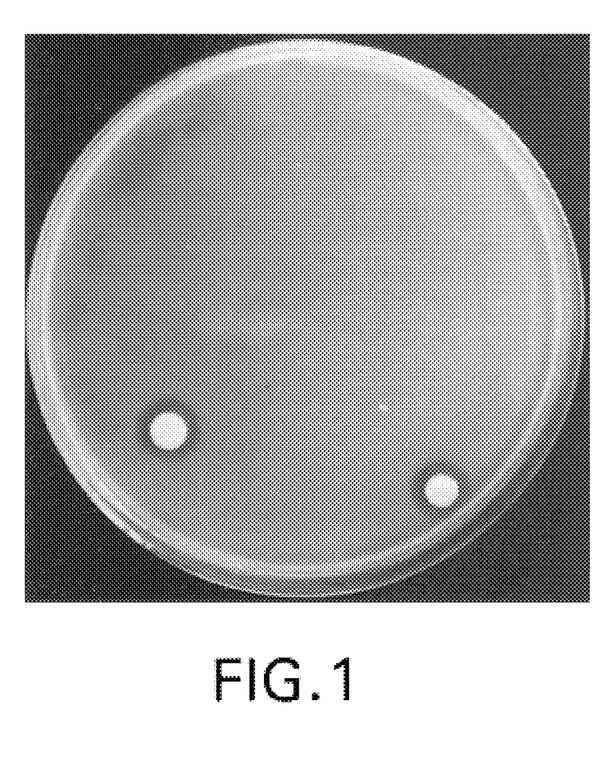
FIG. 1 is a photograph showing the condition of degradation of the polylactic acid resin in the agar plate medium at two weeks following initiation of cultivation of FERM BP-6108.

An agar plate medium containing 1.5% agar was prepared by emulsifying 1,000 mg of a polylactic acid resin (Product Name: "Lacti," manufactured by Shimadzu Corporation; Mw: $1.89 \times 10^5$) in 1 liter of the basal medium shown in Table 2. To this medium, the FERM BP-6108 strain was inoculated, followed by cultivation at 30° C. for 2 weeks. As shown in FIG. 1, a transparent area appeared around each colony formed by the FERM BP-6108 strain on the agar plate medium showing emulsive turbidity.

Example 2

Figure 2:
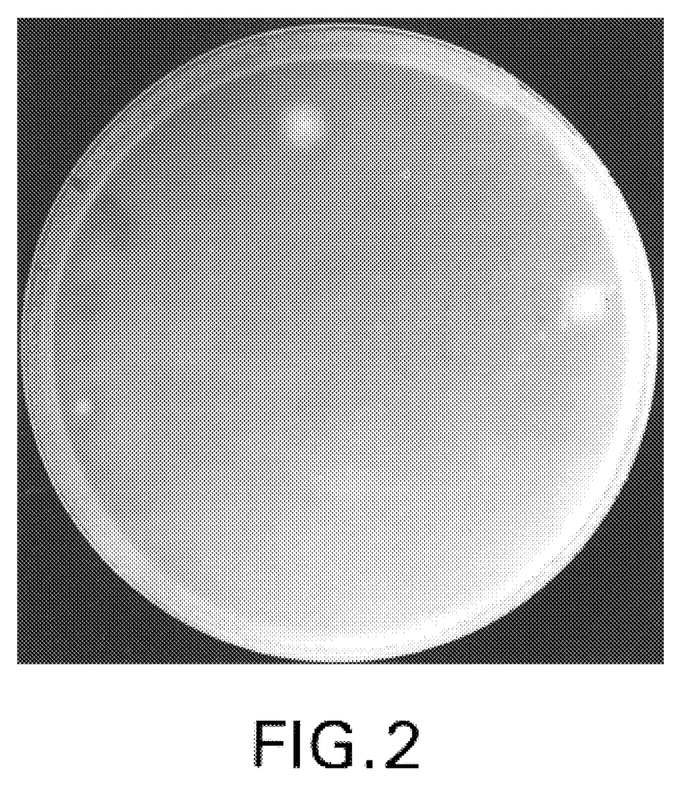
FIG. 2 is a photograph showing the condition of degradation of the polylactic acid resin in an agar plate medium at two weeks following initiation of cultivation of FERM BP-6109.

A medium was prepared by adding 100 mg of a powdered polylactic acid resin (Product Name: "Lacti," manufactured by Shimadzu Corporation; Mw: $1.89 \times 10^5$) as a carbon source to 100 ml of the basal medium shown in Table 2. To this medium, the FERM BP-6109 strain was inoculated, followed by cultivation at 50° C. for 2 weeks. As shown in FIG. 2, a transparent area appeared around each colony formed by the FERM BP-6109 strain on the agar plate medium showing emulsive turbidity.

Example 3

Figure 3:
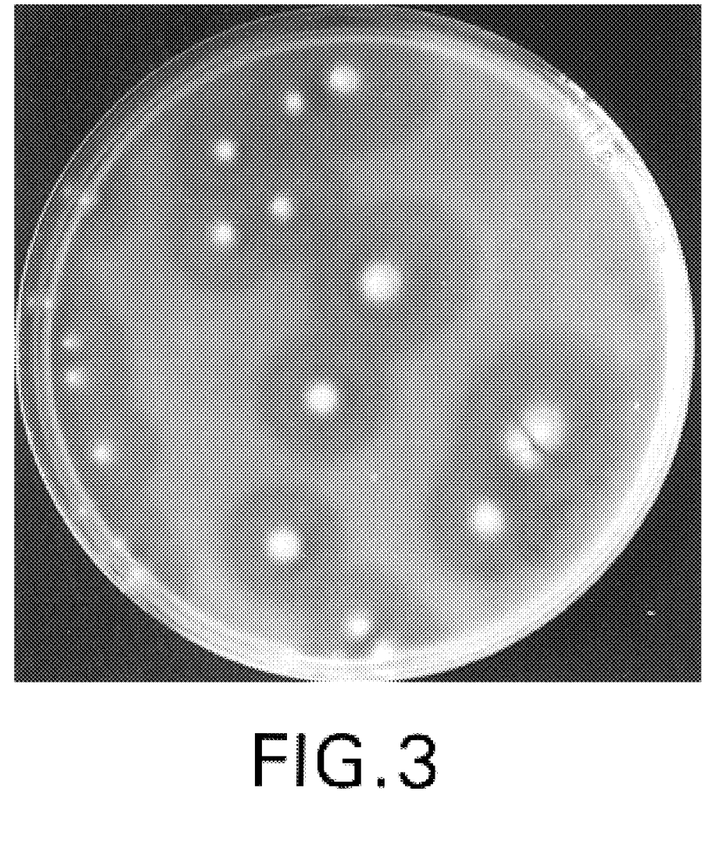
FIG. 3 is a photograph showing the condition of degradation of the polylactic acid resin in an agar plate medium at two weeks following initiation of cultivation of FERM BP-6110.

An agar plate medium containing 1.5% agar was prepared by emulsifying 1,000 mg of a polylactic acid resin (Product Name: "Lacti," manufactured by Shimadzu Corporation; Mw: $1.89 \times 10^5$) in 1 liter of the basal medium shown in Table 2. To this medium, the FERM BP-6110 strain was inoculated, followed by cultivation at 30° C. for 2 weeks. As shown in FIG. 3, a transparent area appeared around each colony formed by the FERM BP-6110 strain on the agar plate medium showing emulsive turbidity.

Example 4

A medium was prepared by adding 100 mg of a powdered polylactic acid resin (Product Name: "Lacti," manufactured by Shimadzu Corporation; Mw: $1.89 \times 10^5$) as a carbon source to 100 ml of the basal medium shown in Table 2. To this medium, the FERM BP-6109 strain was inoculated, followed by cultivation using a rotary shaker at 50° C. and 180 rpm for 2 weeks. The weight change of the polylactic acid resin as a result of degradation of the powdered polylactic acid resin added was determined by chloroform extraction to obtain changes over time in the weight of polylactic acid resin recovered. As shown in Table 7, the weight of the polylactic acid resin decreased by about 10%, while there are almost no weight changes in the control inoculation with no strains between before and after cultivation.

TABLE 7

Change in weight of polyactic acid resin recovered as a result of degradation by FERM BP-6109 strain

| | Recovered Weight (mg) | |
| --- | --- | --- |
| | Before Incubation | After Incubation |
| No Inoculation with FERM BP-6109 | 104.5 | 96.8 |
| Inoculation with FERM BP-6109 | 105.7 | 86.7 |

Example 5

Figure 4A:
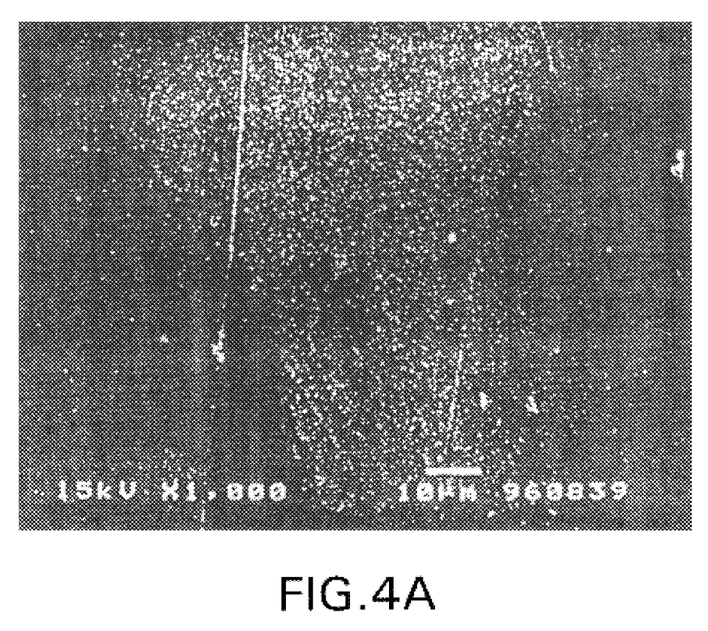
Figure 4B:
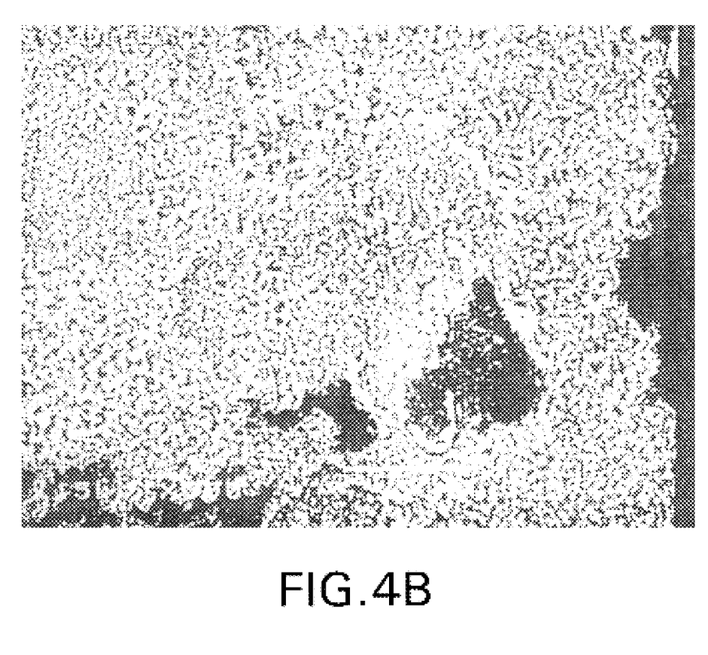

An agar plate medium containing the basal medium shown in Table 2 was prepared. A piece of film prepared from a polylactic acid resin (Product Name: "Lacti," manufactured by Shimadzu Corporation; Mw: $1.89 \times 10^5$) was immersed in a suspension of the FERM BP-6109 strain, placed on the agar plate, and cultured at 50° C. for 40 days. After completion of the cultivation, the piece of film was washed with sterile water, dried in air, and examined using the scanning electron microscope JST-T220 (manufactured by JEOL Ltd.) at a magnification of ×1,000 and an acceleration voltage of 15 kV. As shown in FIG. 4, surface roughness was confirmed.

Example 6

A medium was prepared by adding 100 mg of a powdered polylactic acid resin (Product Name: "Lacti," manufactured by Shimadzu Corporation; Mw: $1.89 \times 10^5$) as a carbon source to 100 ml of the basal medium shown in Table 2. To this medium, the FERM BP-6110 strain was inoculated, followed by cultivation using a rotary shaker at 30° C. and 180 rpm for 4 weeks. The weight change of the polylactic acid resin as a result of degradation of the powdered polylactic acid resin added was determined by chloroform extraction to obtain changes over time in the weight of the polylactic acid resin. As shown in Table 8, the weight of the polylactic acid resin decreased by about 30%, while there was only a little weight change in the control inoculating with no strains between before and after cultivation.

TABLE 8

Change in weight of polyactic acid resin recovered as a result of degradation by FERM BP-6110 strain

| | Recovered Weight (mg) | |
| --- | --- | --- |
| | Before Incubation | After Incubation |
| No Inoculation with FERM BP-6110 | 101.2 | 93.6 |
| Inoculation with FERM BP-6110 | 102.8 | 71.0 |

Example 7

Figure 5A:
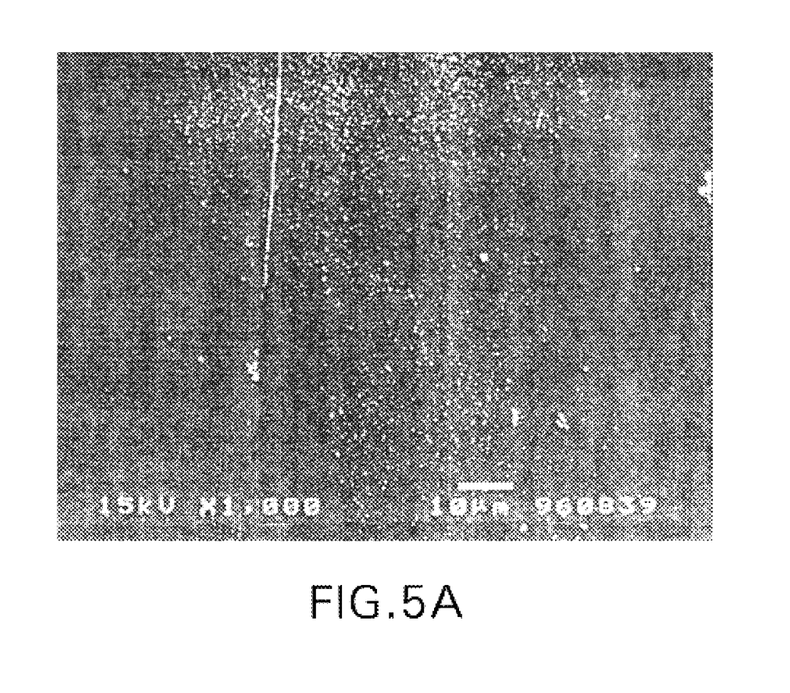
Figure 5B:
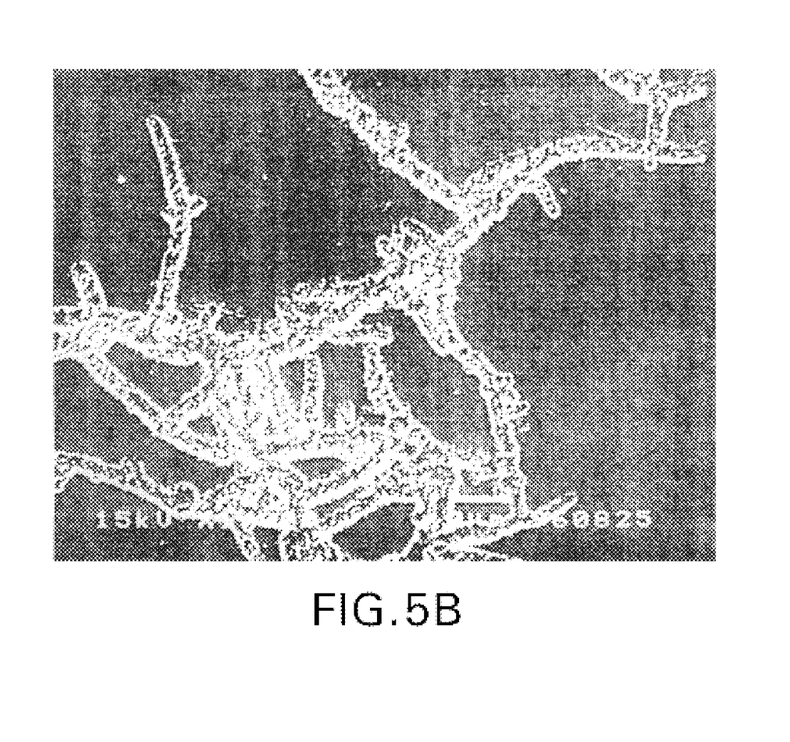

An agar plate medium containing the basal medium shown in Table 2 was prepared. A piece of film prepared from a polylactic acid resin (Product Name: "Lacti," manufactured by Shimadzu Corporation; Mw: $1.89 \times 10^5$) was immersed in a suspension of the FERM BP-6110 strain, placed on the agar plate, and cultured at 30° C. for 40 days.

After completion of the cultivation, the piece of film was washed with sterile water, dried in air, and examined using the scanning electron microscope JST-T220 (manufactured by JEOL Ltd.) at a magnification of ×1,000 and an acceleration voltage of 15 kV. As shown in FIG. 5, surface roughness was confirmed.

These findings demonstrate that the strains isolated in the present invention are capable of degrading a high-molecular polylactic acid resin.

Experimentation with FERM BP-6111 in the same manner as above yielded results similar to those obtained with FERM BP-6110.

The present invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. An isolated microorganism belonging to the genus Streptomyces which is capable of degrading a polylactic acid resin and deposited under accession No. FERM BP-6110 as *Streptomyces violaceusniger* or deposited under accession No. FERM BP-6111 as *Streptomyces cyaneus*.

2. The microorganism according to claim 1, wherein said *Streptomyces violaceusniger* is *Streptomyces violaceusniger* deposited under accession No. FERM BP-6110.

3. The microorganism according to claim 1, wherein said *Streptomyces cyaneus* is *Streptomyces cyaneus* deposited under accession No. FERM BP-6111.

4. A method of degrading a polylactic acid resin comprising a step of culturing a microorganism capable of degrading a polylactic acid resin in a medium containing a polylactic acid resin, wherein said microorganism is a microorganism belonging to the genus Streptomyces and deposited under accession No. FERM BP-6110 as *Streptomyces violaceusniger* or deposited under accession No. FERM BP-6111 as *Streptomyces cyaneus*.

5. The method according to claim 4, wherein said *Streptomyces violaceusniger* is *Streptomyces violaceusniger* deposited under accession No. FERM BP-6110.

6. The method according to claim 4, wherein said *Streptomyces cyaneus* is *Streptomyces cyaneus* deposited under accession No. FERM BP-6111.

* * * * *